United States Patent [19]

Ueno et al.

[11] Patent Number: 5,274,130
[45] Date of Patent: Dec. 28, 1993

[54] PROCESS FOR PRODUCTION OF PROSTAGLANDIN INTERMEDIATES

[75] Inventors: Ryuji Ueno, Nishinomiya; Tomio Oda, Sanda, both of Japan

[73] Assignee: R-Tech Ueno Ltd., Osaka, Japan

[21] Appl. No.: 937,949

[22] Filed: Sep. 1, 1992

[30] Foreign Application Priority Data

Sep. 3, 1991 [JP] Japan .................. 3-222704

[51] Int. Cl.$^5$ .......................... C07D 311/00
[52] U.S. Cl. ....................... 549/355; 549/396
[58] Field of Search ............... 549/355, 396

[56] References Cited

U.S. PATENT DOCUMENTS 3,933,898 1/1976 Nelson ................. 549/422
4,259,481 3/1981 Johnson ............... 549/426

OTHER PUBLICATIONS

Journal of Medicinal Chemistry, vol. 21, No. 5, pp. 443–447, 1978.
Chem. Pharm. Bull. 28(5), 1422–1431 (1980).

*Primary Examiner*—C. Warren Ivy
*Assistant Examiner*—Raymond Covington
*Attorney, Agent, or Firm*—Sughrue, Mion, Zinn, Macepeak & Seas

[57] ABSTRACT

The isomer ratio of a cis-isomer against the corresponding trans-isomer with respect to the 5-6 double bond is improved in the production of prostaglandins, when a lactol is reacted with an ylide to cause simultaneously formation of the 5-double bond and an α-chain, whereby the ylide generated from a phosphonium salt with a potossium base, and a solvent which is liquid at the reaction temperature and has a dipole moment of 0.3 to 3.0D are used.

4 Claims, No Drawings

PROCESS FOR PRODUCTION OF PROSTAGLANDIN INTERMEDIATES

BACKGROUND OF THE INVENTION

The present invention relates to a process for the production of prostaglandin intermediates.

A prostaglandin has a basic skeleton represented by the formula (c):

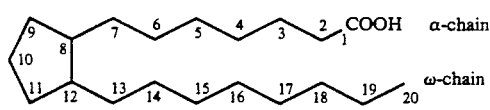

A prostaglandin having a double bond between the carbon atoms of the 5 and 6 positions (referred to as the $C_5-C_6$ position hereinafter, and this compound is hereinafter referred to as $\Delta^5$-PG), of which carbon atoms are located at the 2nd and 3rd positions counted from the carbon atom of the 5 membered ring having the α-chain linked thereto, has the cis- and trans-isomers. As the compound having a physiological activity is mainly a cis-isomer, it is important from the industrial standpoint to produce the cis-isomer in improved yield.

Up to this time the introduction of the α-chain in the production of prostaglandins has been achieved as illustrated is the following scheme using Wittig reaction in which an ylide reacts with the lactol (d) having the ω-chain introduced therein:

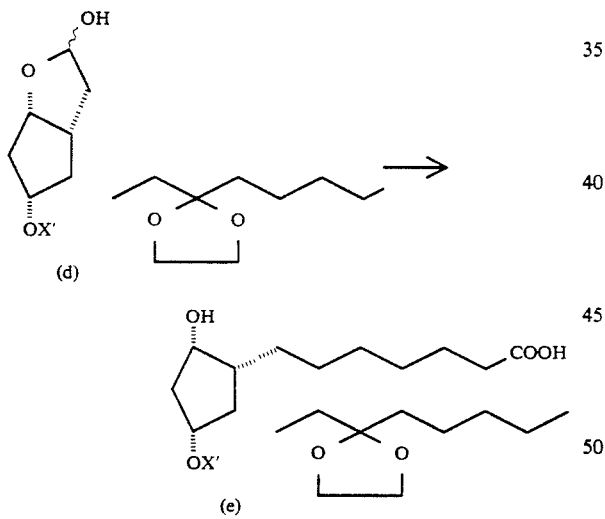

wherein X' is a protective group.

In order to obtain $\Delta^5$-PGs which have a double bond between the $C_5-C_6$ positions the lactol (d) is reacted with the ylide obtained from (4-carboxybutyl)triphenylphosphonium bromide, which is usually used in the form of a sodium salt of carboxylic acid produced by the reaction of (4-carboxybutyl)triphenylphosphonium bromide with sodium methylsulfinyl carbanion being obtainable from DMSO and NaH:

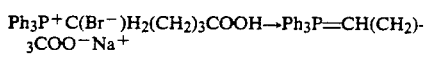

This ylide is reacted with the lactol in a solvent such as DMSO and the like. The reaction temperature is generally in the range from the ambient temperature to 70° C.

According to the above process which has conventionally been used for the introduction of the α-chain, the trans type $\Delta^5$-PGs (referred to as $\Delta^5$-trans-PGs) is present in the resultant product at a rate of about 10% by weight. Consequently, it is absolutely necessary to purify the product when it is used as a starting material for drugs. In such purification the more impurity makes the less productivity.

SUMMARY OF THE INVENTION

The present invention relates to a process for production of prostaglandin intermediates.

In order to improve the yield of $\Delta^5$-cis-PGs which exhibit physiological activities, use is made of the ylide from a phosphonium salt and potassium base as well as an organic reaction solvent which is liquid at employed reaction temperature and shows a dipole moment of 0.3 to 3.0D.

DETAILED DESCRIPTION OF THE INVENTION

The present invention relates to a process for the production of prostaglandin intermediates which comprises reacting a lactol represented by the following formula (I) or (I'):

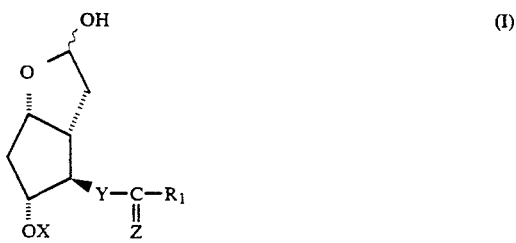

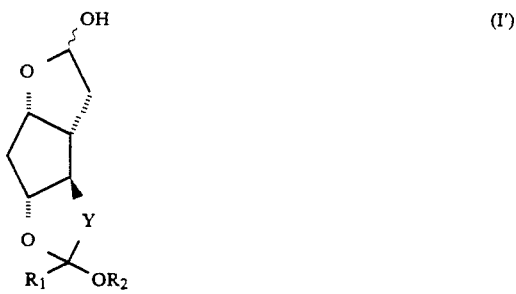

in which Y represents $—CH_2—H_2—$, $—CH=CH—$, $—CH_2—CH_2—CH_2—$, $—CH_2—CH=CH—$ or $—CH=CH—CH_2—$ (in case of the formula (I') and Y being one of olefinic groups, Y represents cis-form one); $R_1$ represents a saturated or unsaturated aliphatic, alicyclic, aromatic, alkoxyalkyl, or aryloxyalkyl group either of which a number of carbon atoms of 1 to 12 and may have one or more substituent(s); $R_2$ represents an alkyl group having a number of carbon atoms of 1 to 4; Z represents a group which forms a cyclic acetal in cooperation with the carbon atom having Z attached thereto; and X represents a hydrogen atom or a group represented by the formula (a):

in which $R_3$ and $R_4$ represent independently a hydrogen atom or a $C_1-C_4$ alkyl group; and $R_5$ represents a $C_1-C_4$ alkyl, cyclohexyl, phenyl or benzyl group ($R_4$ and $R_5$ may cooperate with the other to form a ring), and an ylide represented by formula (II):

$$Ph_3P=CH-Q-COO^-K^+ \quad (II)$$

in which Ph represents a phenyl group,; Q represents a saturated or unsaturated hydrocarbon group having a number of carbon atoms of 2 to 6 which may have one or more substituent(s),
in an ethereal or aromatic solvent having a melting point of lower than $-25°$ C. and a dipole moment of 0.3–3.0D.

The feature of the present invention is in the use of a potassium carboxylate as an ylide and the selection of a specifically determined solvent. The reduction in ratio of the trans-isomer is not observed when the DMSO which is conventionally the most commonly employed solvent for this reaction, is used as the solvent, even if a potassium carboxylate is used as an ylide, and such reduction is not observed as well, either when a lithium salt or a sodium carboxylate is used as the ylide, even if the solvent specified in the present invention is used.

The lactol used in the present invention is represented by the formula (I) or (I'):

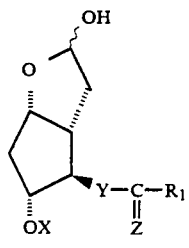

(I)

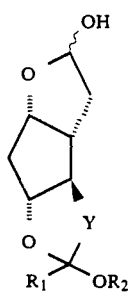

(I')

in which Y represents $-CH_2-CH_2-$, $-CH=CH-$, $-CH_2-CH_2-CH_2-$, $-CH_2-CH=CH-$ or $-CH=CH-CH_2-$ (in case of the formula (I') and Y being one of olefinic groups, Y represents cis-form one);.

$R_1$ is not restrictive, but may include any alkyl groups which are common in the ω-chains of prostaglandins. Typical examples of the groups are aliphatic, alicyclic, or aromatic groups, either of which have a number of carbon atoms of 1 to 12. A preferable aliphatic group is a saturated one which has a number of carbon atoms of 2 to 10, and more preferable one is a saturated hydrocarbon group which has a number of carbon atoms of 5 to 7. Examples of the substituents are methyl, ethyl, hydroxyl, methoxy, ethoxy, fluorine, chlorine and the like. Examples of the alicyclic hydrocarbon groups are cyclopropenyl, cyclopentyl, cyclohexyl and the like, which may be alkyl alicyclic groups such as alkylcyclopentyl. Examples of the aromatic groups are phenyl, tolyl, and the like, which may include aralkyl group such as benzyl and the like. $R_1$ may be an alkoxyalkyl group such as ethoxybutyl; an aryloxyalkyl group such as phenoxybutyl and the like.

Substitution on the group $R_1$ or presence a double bond thereon does not exert any substantial influence on the isomer ratio of $\Delta^5$-cis-PGs against $\Delta^5$-trans PGs.

$R_2$ is generally a $C_1$–$C_4$ alkyl group which may be branched, but it is not restrictive.

Z is a commonly used protective groups for the oxo group at the 15-position in the synthetic process of prostaglandins, and typically such groups as may fuse to the carbon atom at the 15- or 16-position in the ω-chain having Z attached to form a cyclic acetal. Specific examples of the cyclic acetals are exemplified as follows:

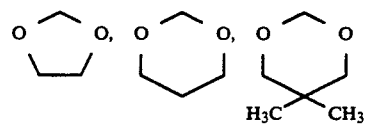

X is a hydrogen atom or a protective group which is commonly used for protecting the hydroxyl group at the 11-position in the synthetic process of prostaglandins, typically a group represented by the following formula (a):

$$R_5OC(R_3)(R_4)- \quad (a)$$

wherein the groups $R_3$ and $R_4$ are independently a hydrogen atom or an alkyl group having a number of carbon atoms of 1 to 4 which may be branched; and $R_5$ may be an alkyl group having a number of carbon atoms of 1 to 4, cyclohexyl, phenyl, benzyl group and the like, which may have one substituent(s) or more such as halogen atom or an alkoxy group and the like. $R_4$ and $R_5$ each may fuse to the other to form a ring.

The examples of X may be tetrahydropyranyl, methoxymethyl, t-butoxymethyl, 1-ethoxyethyl, 1-methoxy-1-methylethyl, benzyloxymethyl, 2-methoxyethoxymethyl, 2,2,2-trichloroethoxymethyl, and the like.

The ylide (II) used in the present invention, represented by the following formula:

$$Ph_3P=CH-Q-COO^-K^+ \quad (II)$$

wherein Ph and Q are as defined above can be obtained, for instance, by the reaction of a phosphonium salt (III) represented by the formula:

$$[Ph_3P^+CH_2-Q-COOH](Hal)^- \quad (III)$$

wherein Ph and Q are as defined above, and Hal is a halogen atom, especially Br, Cl or I, with a suitable potassium base such as potassium t-butoxide, potassium hydride, potassium bis(trimethylsilyl)amide, potassium methoxide, potassium ethoxide, potassium n-butoxide and the like in an appropriate solvent. A sodium base has been conventionally used generate the ylide, but it has been found that a potassium base is essential for preparing the $\Delta^5$-cis-PGs.

The solvent used for the preparation of this ylide is not restrictive, but it is advantageous to use the same solvent as the solvent used in the next reaction between the ylide and the compound (I) or (I'), because the ylide solution obtained can be used as such in the next reaction.

The resultant ylide (II) is reacted with the lactol represented by the formula (I) or (I') in an aromatic or ethereal solvent, which has a melting point of lower than −25 ° C., and a dipole moment of 0.3 to 3.0D. The reaction temperature is suitably in the range of about −25 ° C. to −40° C. If it is higher than −25 ° C., the production ratio of Δ⁵-cis-PGs to Δ⁵-trans-PGs becomes lower.

The solvent used in the present invention has necessarily a melting point lower than the reaction temperature. The isonomer ratio and yield of Δ⁵-cis-PGs decrease when a solvent having a dipole moment lower or higher than the aforementioned range is used. A suitable solvent is ethereal or aromatic, and in the case of the former the dipole moment is more preferably 1.0 to 2.0, and in case of the latter it is more preferably 0.3 to 1.0.

Specific examples of a preferable solvent used for the present invention include tetrahydrofuran (1.70D, mp: −108.5 ° C.), diethyl ether (1.12D, mp: −116.3 ° C.), dibutyl ether (1.22D, mp: −98 ° C.), diisopropyl ether (1.22D, mp: −85.89 ° C.), dimethoxy ethane (1.79D, mp: −58 ° C.), toluene (0.37D, mp: −94.99 ° C.), ethylbenzene (0.58D, mp: −95 ° C.), cumene (0.65D, mp: −96 ° C.) and the like. The particularly preferable solvent is tetrahydrofuran.

The production ratio and the yield of Δ⁵-cis-PGs can be more improved by the combination of the aforementioned ethereal or aromatic solvent with an urea compound represented by the formula (b):

$$(R_6)(R_7)N-CO-N(R_8)(R_9) \quad \text{(b)}$$

wherein $R_6$, $R_7$, $R_8$ and $R_9$ independently represent an alkyl group having a number of carbon atoms of 1 to 2 the $R_7$ and $R_8$ each may cooperate with the other to form a ring.

Typical examples of the urea compounds are 1,3-dimethyl-3,4,5,6-tetrahydro-2(1H)pyrimidine (DMPU), 1,3-dimethyl-2-imidazolidinone (DMEU), 1,1,3,3-tetramethyl urea, 1,1,3,3-tetraethyl urea and the like. These urea compounds may be used in the amount of not more than 50% by volume based on the total volume of solvent, usually 1 to 50% by volume, more preferably 3 to 10% by volume. The dipole moment and the melting point of the urea compounds themselves are not restrictive, but the melting point of the mixed solvent containing the urea compound should be lower than the reaction temperature.

In the case where X is a hydrogen atom, the above urea compounds are preferably used.

The solvent should be used in the amount sufficient to homogeneously dissolve the ylide (II) and the lactol (I) or (I') at the reaction temperature. It is used generally at a ratio of 5 to 100 ml per one gram of the lactol (I) or (I').

The reaction between the lactol (I) or (I') and the ylide (II) is illustrated below:

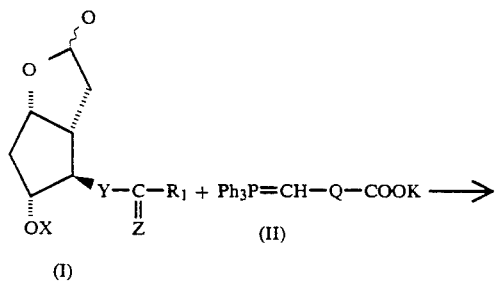

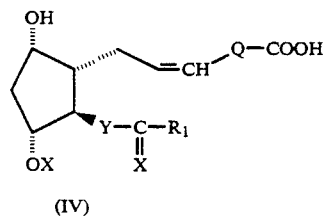

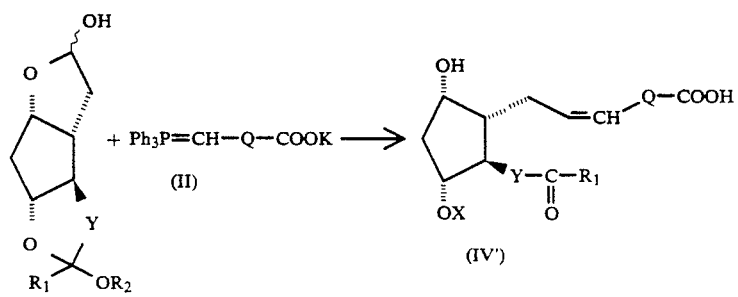

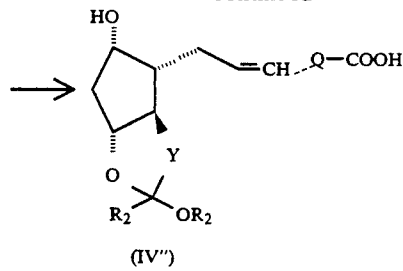

(IV''')

wherein X, Y, Z, $R_1$, $R_2$, $Ph_3$ and Q are defined above.

Various kinds of prostaglandins and derivatives thereof can be prepared from the prostaglandin intermediates of the present invention in the conventional manner. Particularly, the intermediates are the useful for the raw materials of for the preparation of prostaglandins $A_2$, $D_2$, $E_2$, $F_2$ and $J_2$, and their various derivatives.

The Examples are to be illustrated below to describe this invention more specifically.

EXAMPLE 1

Preparation of 13,14-dihydro-20-ethyl-15-keto-$PGF_{2\alpha}$ isopropyl ester (4)

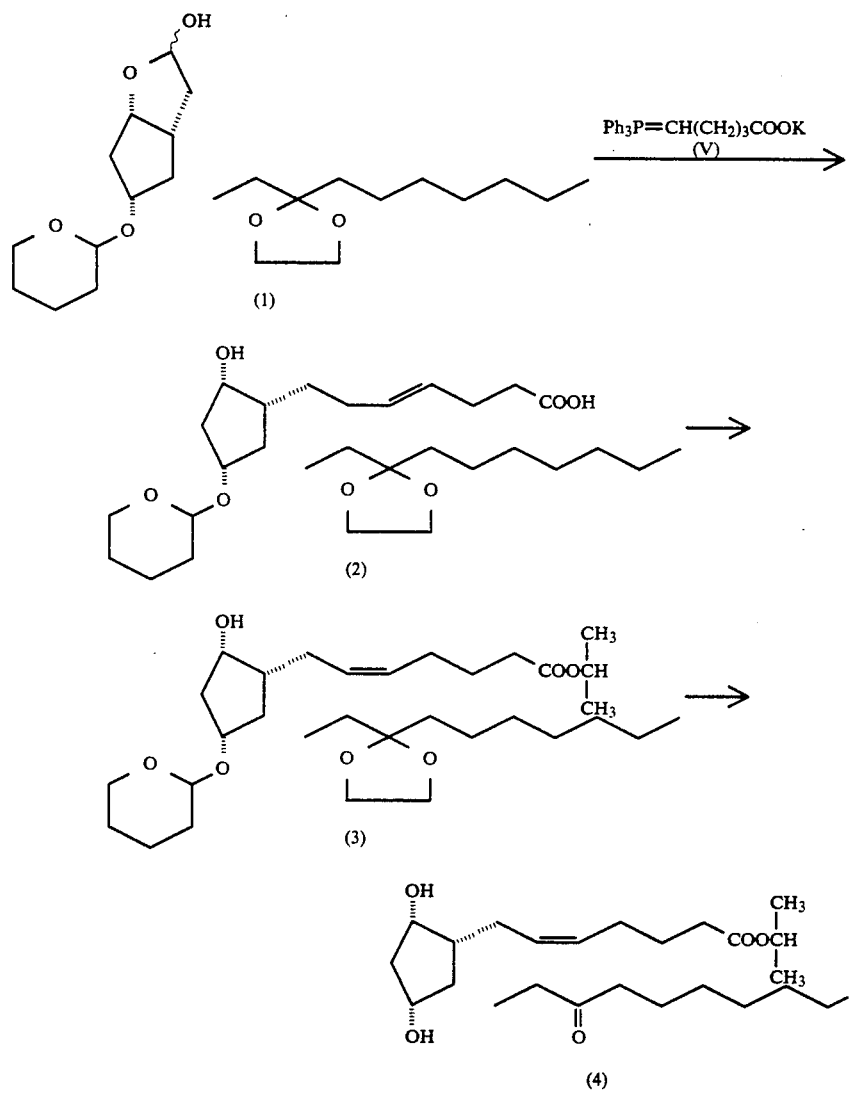

A suspension of (4-carboxybutyl)triphenylphosphonium bromide (1.03 g, 2.32 mmol) in tetrahydrofuran (THF) (0.4 ml) was added in a 100 ml round bottomed flask, into which potassium t-butoxide (1.0M, 4.64 ml, 4.64 mmol) was added dropwise, and stirred for 30 minutes. The reaction mixture was cooled to $-78°$ C., and then a solution of the lactol (1) (0.247 g, 0.58 mmol) in THF (2 ml) was added dropwise over 30 minutes, and warmed to −40 °C. over 6 hours. The reaction mixture was further stirred at −40 °C. for 17 hours. After the usual work-up the crude carboxylic acid (2) was obtained. Yield: 0.387 g.

The reaction product was esterified using DBU (0.26 ml) and isopropyl iodide (0.17 ml) in a dry acetonitrile (5 ml) to give an isopropyl ester (3), and the resultant was hydrolyzed with acetic acid to give 13,14-dihydro-20-ethyl-15-keto-PGF$_2\alpha$ isopropyl ester (4). Yield: 0.1906 (94%). The content of Δ$^5$-trans-isomer in the compound (4) was 1.4%.

The same experiment was repeated by 12 times, and the ratios of the trans-isomer were resulted in the range of 1.1 to 3.5% in the compound (4).

EXAMPLE 2

Preparation of 13,14-dihydro-20-ethyl-15-keto-PGF$_2\alpha$ isopropyl ester (4)

4-Carboxybutyltriphenylphosphonium bromide (1.03 g, 2.32 mmol) and DMPU (1.6 ml) were added into a 100 ml round bottomed flask, into which potassium t-butoxide (1.0M, 4.64 ml, 4.64 mmol) was added and stirred for 30 minutes. After the mixed solution was cooled at −35 °C., a solution (0.45 ml) of the lactol (1) (0.247 g, 0.58 mmol) in a solvent mixture of THF and DMPU (THF/DMPU=3/1) (0.45 ml) and the solvent mixture of THF and DMPU (THF/DMPU=3/1) (0.45 ml) used to wash the vessel of the lactol solution were added dropwise over 20 minutes. The reaction mixture was stirred for 15 hours. After the usual work-up, the crude carboxylic acid (2) was obtained. Yield: 1.21 g.

The crude carboxylic acid (2) (1.21 g) was esterified using DBU (0.26 ml) and isopropyl iodide (0.17 ml) in dry acetonitrile (5 ml) to give isopropyl ester (3). Yield: 0.2945 g (92%).

The isopropyl ester (3) was hydrolyzed with an acid to give 13,14-dihydro-20-ethyl-15-keto-PGF$_2\alpha$ isopropyl ester (4). Yield: 0.2080 g, (92%). The content of Δ$^5$-trans-isomer was 1.1%

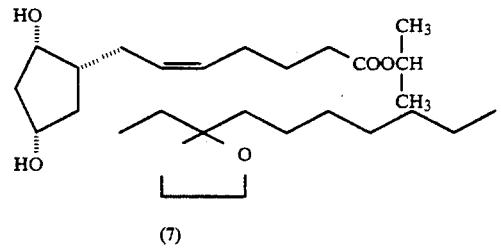

(7)

Preparation
13,14-dihydro-20-ethyl-15,15-ethylenedioxy-PGF$_2\alpha$ isopropyl ester (7)

Dry THF (70 ml) was added into a four-neck flask, and potassium t-butoxide (9.31 g) was suspended in the THF under algon atmosphere. To the suspention were added (4-carboxybutyl)triphenylphosphonium bromide (17.5 g) and DMPU (2.12 ml), followed by stirring for one hour. The reaction mixture was cooled to −35 °C., followed by addition of a solution of the lactol (5) (3.00g) in dry THF (60 ml) cooled at −35 °C. The vessel of the lactol (5) was washed with THF (10 ml), and the wash was added to the reaction mixture. The reaction was stirred for 20.5 hours and the bath was gradually warmed to −10 °C. during the reaction. After the usual work-up the crude carboxylic acid (6) was obtained. Yield: 4.22 g.

The crude carboxylic acid (6) (4.22 g) was esterified using DBU (8.87 ml) and isopropyl iodide (2.96 ml) in dry acetonitrile (21 ml) to give the isopropyl ester (7). Yield: 3.70 g (90.1%). The content of Δ$^5$-trans-isomer in the compound (7) was 3.3%.

EXAMPLE 3

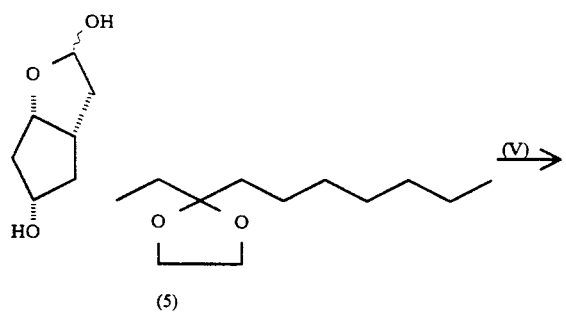

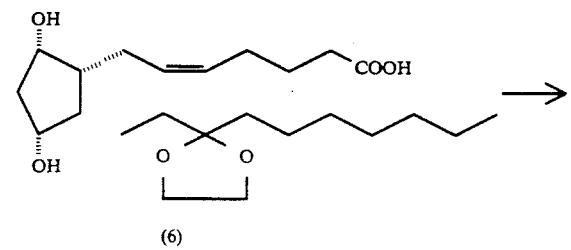

EXAMPLE 4

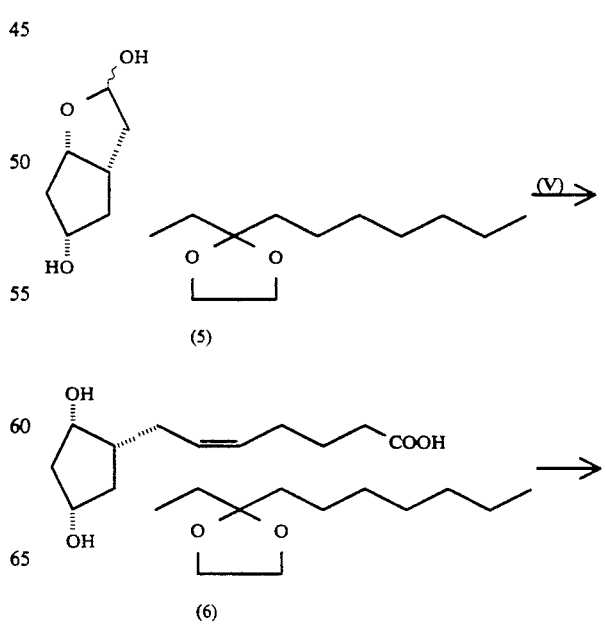

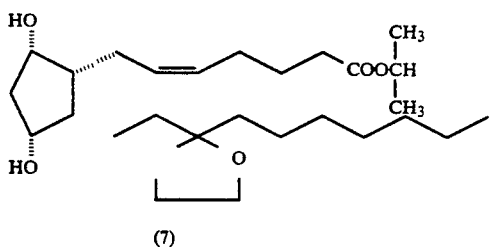

(7)

Preparation of
13,14-dihydro-20-ethyl-15,15-ethylenedioxy-PGF$_{2\alpha}$
isopropyl ester (7)

The same manners and the same conditions employed in the Example 3 were carried out except that the loctol (5) (2.15 g) and DMEU (1.37 ml) were used, to give the ester (7). Yield: 2.48 g (84.3%, in two steps). The isomer ratio of $\Delta^5$-trans-isomer against $\Delta^5$-cis-isomer was 3.1%.

The trans/cis ratio was determined by measuring the each peak area of the cis and the trans isomers separated by the HPLC using an ultraviolet spectrophotometer. The correction of the ratio based on their adsorption coefficients was not made.

EXAMPLE 5

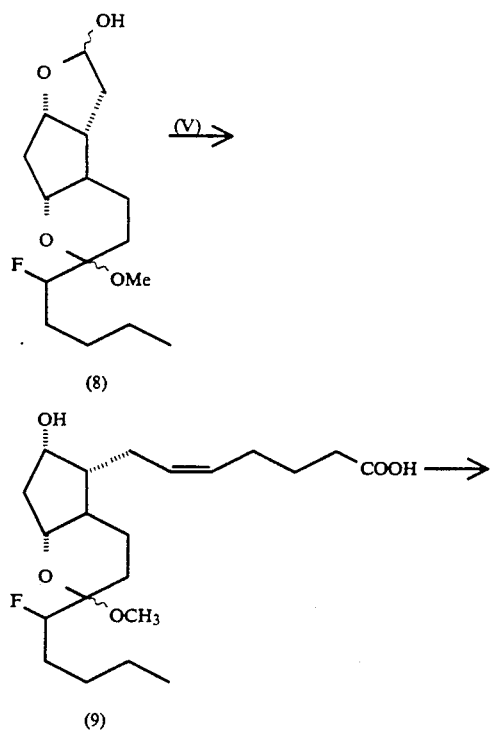

(8)

(9)

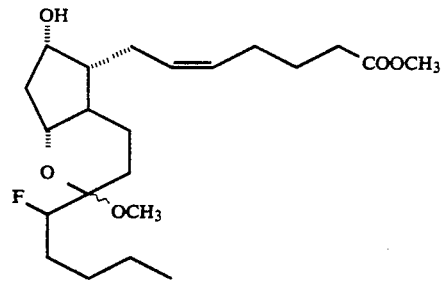

(10)

Preparation of Methyl (Z)-7-{(4aR, 5R, 6s, 7aR)-2-[1(Rs)-fluoropentyl]-6-hydroxy-2-methoxyperhydrocyclopenta[b]-pyran-5-yl}hept-5-enoate(10)

(4-Carboxybutyl)triphenylphosphonium bromide (6.00 g) was suspended in dry THF (10 ml), followed by addition of a solution of potassium t-butoxide (3.35 g) in THF (35 ml), and stirring at room temperature for 30 minutes. The reaction mixture was cooled to −40° C., and the solution of the lactol (8) (0.821 g) in THF (15 ml) was added. The reaction mixture was slowly warmed to −20° C. and the mixture was stirred for 3 hours. The carboxylic acid (9) obtained by the usual work-up was esterified with diazomethane, and the resultant was chromatographed on a silica gel column to give a methyl ester (10). Yield: 0.928 g (85%). The content of $\Delta^5$-trans-isomer in the compound (10) was found to be 0.6%.

EXAMPLE 6

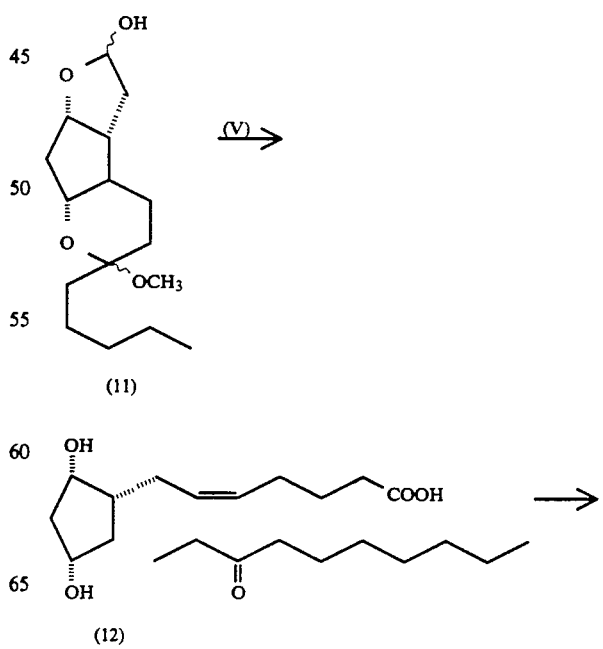

(11)

(12)

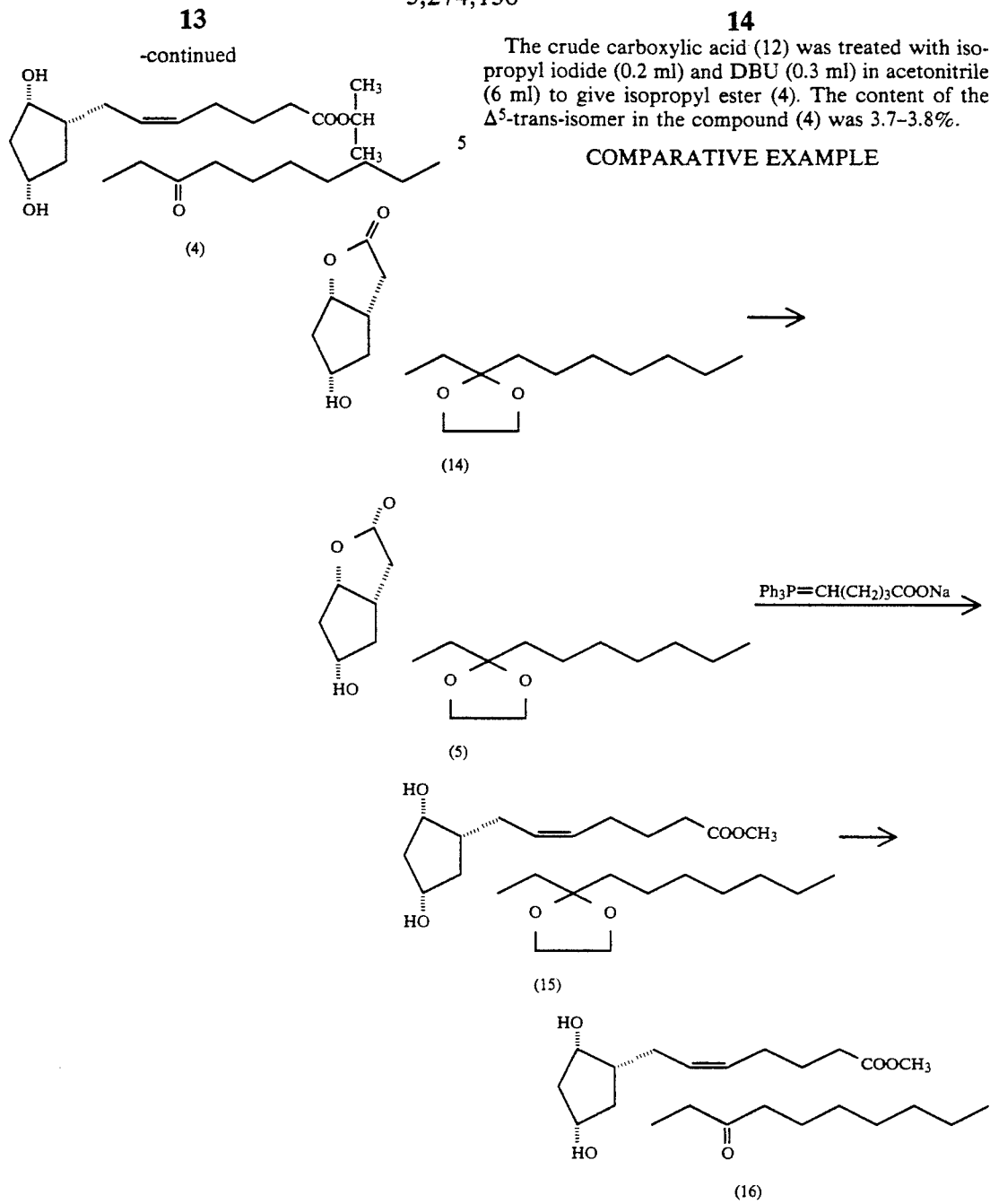

The crude carboxylic acid (12) was treated with isopropyl iodide (0.2 ml) and DBU (0.3 ml) in acetonitrile (6 ml) to give isopropyl ester (4). The content of the $\Delta^5$-trans-isomer in the compound (4) was 3.7–3.8%.

COMPARATIVE EXAMPLE

Preparation of 13,14-dihydro-20-ethyl-15-keto-PGF$_2\alpha$ methyl ester (16)

The lactone (14) (1.22 g) was reduced by DIBAL-H (7.6 ml) at −78 °C. in dry toluene (30 ml). After stirring for 45 minutes, methanol (10 ml) was added, followed by stirring for 80 minutes. Ether was then added to the reaction solution. The reaction mixture was filtered, and the filtrate was concentrated under reduced pressure to give the lactol (5).

Separately, sodium hydride (60 % dispersion in mineral oil, 1.15 g) washed with dry ether was suspended in dry DMSO (30 ml), and then heated at 65–70 °C. for one hour. After the resultant was cooled to room temperature, a solution of (4-carboxybutyl)triphenylphosphonium bromide (6.4 g) in DMSO was added, followed by stirring for 40 minutes. Into the resultant solution was added dropwise a solution of the lactol (5)

Preparation of 13,14-dihydro-20-ethyl-15-keto-PGF$_2\alpha$ isoprpyl ester (4)

A solution of potassium t-butoxide (0.517 g, 4.61 mmol) in THF (3ml) was added dropwise into the suspension of (4-carboxybutyl)triphenylphosphonium bromide (1.022 g, 2.30 mmol) in THF (2ml), followed by stirring for one hour. The resultant was cooled to −40° C., into which the lactol (11) (0.180 g, 0.58 mmol) solution in THF (2ml) was added dropwise. The reaction was warmed to −20° C. over one hour. The mixture was stirred at −15° C. for 15 hours. The carboxylic acid (12) was obtained by the usual work-up. Yield: 0.2578 g.

in DMSO. The reaction mixture was stirred overnight. The usual work-up gave a carboxylic acid (6). The carboxylic acid (6) was esterified with diazomethane to give a methyl ester (15), which was then purified with silica gel column. Yield: 1.29 g (82%)

The methyl ester (15) (1.06 g) was dissolved in a solvent mixture of acetic acid, water, and THF (3:1:1) (18 ml), and the solution was then kept at 50° C. for 3 hours. After the usual work-up, 13,14-dihydro-20-ethyl-15-keto-PGF$_2\alpha$ methyl ester (16) was obtained. Yield: 0.868 g (74%). The content of $\Delta^5$-trans-isomer in the compound (16) was found to be 9.3%.

What is claimed is:

1. A process for the production of prostaglandin intermediates which comprises reacting a lactol represented by the following formula (I) or (I'):

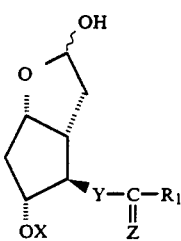

(I)

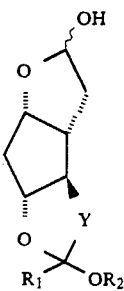

(I')

in which Y represents —CH$_2$—CH$_2$—, —CH=CH—, —CH$_2$—CH$_2$—CH$_2$—, —CH$_2$—CH=CH— or —CH=CH—CH$_2$— with the proviso that when Y represents —CH=CH— or —CH$_2$—CH=CH— in formula (I'), the double-bond of —CH=CH— and of —CH$_2$—CH=CH— is of the cis form R$_1$ represents a saturated or unsaturated aliphatic, alicyclic, aromatic, alkoxyalkyl, or aryloxyalkyl group, either which have a number of carbon atoms of 1 to 12 and may have one or more substituent(s); R$_2$ represents an alkyl group having a number of carbon atoms of 1 to 4; Z represents a group which forms a cyclic acetal together with the carbon atom to which Z attaches; and X represents a hydrogen atom or a group represented by the formula (a):

$$R_5OC(R_3)(R_4)—$$ (a)

in which R$_3$ and R$_4$ represent independently a hydrogen atom or an alkyl group having a number of carbon atoms of 1 to 4; and R$_5$ represents an alkyl group having a number of carbon atoms of 1 to 4, cyclohexyl, phenyl or benzyl group (R$_4$ and R$_5$ each may fuse to the other to form a ring), and an ylide represented by the formula (II):

$$Ph_3P=CH—Q—COO^{31} K^+$$ (II)

in which Ph represents a phenyl group,; Q represents a saturated or unsaturated hydrocarbon group having a number of carbon atoms of 2 to 6 which may have one or more substituent(s), in an ethereal or aromatic solvent having a melting point of lower than −25° C. and a dipole moment of 0.3–3.0D.

2. The process of the claim 1, in which the solvent is selected from the group consisting of tetrahydrofuran, diethyl ether, dipropyl ether, diisopropyl ether and toluene.

3. The process of the claim 1, in which the reaction is carried out at a temperature of from −25° C. to −40° C.

4. The process of claim 1, in which in addition to the ethereal or aromatic solvent a urea compound represented by the formula (b) is present:

$$(R_6)(R_7)N—CO—N(R_8)(R_9)$$ (b)

in which R$_6$, R$_7$, R$_8$ and R$_9$ represent an alkyl group having a number of carbon atoms of 1 to 2 (R$_7$ and R$_8$ each may cooperate with the other to form a ring).

* * * * *